United States Patent [19]
Beck et al.

[11] Patent Number: 5,382,737
[45] Date of Patent: Jan. 17, 1995

[54] SELECTIVE ETHYLBENZENE DISPROPORTIONATION PROCESS (SEBDP) WITH EX SITU SELECTIVATED ZEOLITE CATALYSTS

[75] Inventors: Jeffrey S. Beck, Princeton, N.J.; Sharon B. McCullen, Newtown, Pa.; David H. Olson, Pennington; Chaya R. Venkat, Princeton, both of N.J.

[73] Assignee: Mobil Oil Corp., Fairfax, Va.

[21] Appl. No.: 69,257

[22] Filed: May 28, 1993

[51] Int. Cl.$^6$ ............................................. C07C 5/52
[52] U.S. Cl. .................................... 585/475; 585/470
[58] Field of Search ..................... 585/475, 467, 470

[56] References Cited

U.S. PATENT DOCUMENTS

| | | | |
|---|---|---|---|
| 3,257,310 | 6/1966 | Plank et al. | 208/120 |
| 3,437,587 | 4/1969 | Elbert et al. | 208/120 |
| 3,682,996 | 8/1972 | Kerr | 260/448.8 R |
| 3,698,157 | 10/1972 | Allen et al. | 260/674 |
| 4,016,218 | 4/1977 | Haag et al. | 260/671 R |
| 4,060,568 | 11/1977 | Rodewald | 585/640 |
| 4,086,287 | 4/1978 | Kaeding et al. | 260/671 R |
| 4,090,981 | 5/1978 | Rodewald | 252/455 Z |
| 4,100,215 | 7/1978 | Chen | 260/671 M |
| 4,117,024 | 9/1978 | Kaeding | 260/671 R |
| 4,127,616 | 11/1978 | Rodewald | 260/671 R |
| 4,145,315 | 3/1979 | Rodewald | 252/455 Z |
| 4,224,141 | 9/1980 | Morrison et al. | 208/120 |
| 4,283,306 | 8/1981 | Herkes | 252/432 |
| 4,326,994 | 4/1982 | Haag et al. | 252/455 Z |
| 4,402,867 | 9/1983 | Rodewald | 252/455 |
| 4,443,554 | 4/1984 | Dessau | 502/71 |
| 4,465,886 | 8/1984 | Rodewald | 585/467 |
| 4,477,583 | 10/1984 | Rodewald | 502/71 |
| 4,487,843 | 12/1984 | Telford et al. | 502/85 |
| 4,522,929 | 6/1985 | Chester et al. | 502/77 |
| 4,548,914 | 10/1985 | Chu | 502/85 |
| 4,559,314 | 12/1985 | Shihabi | 502/71 |
| 4,843,057 | 6/1989 | D'Amore et al. | 502/263 |
| 4,851,604 | 7/1989 | Absil et al. | 585/475 |
| 4,927,979 | 5/1990 | Yamagishi et al. | 568/791 |
| 4,950,835 | 8/1990 | Wang et al. | 585/467 |
| 5,173,461 | 12/1992 | Absil et al. | 502/62 |

FOREIGN PATENT DOCUMENTS

0296582A2  6/1988  European Pat. Off. .

OTHER PUBLICATIONS

Nakajima et al., "p-Xylene-Selective Disproportionation of Toluene over a Modified Pentasil Type Zeolite", *Sekiyu Gakkaishi*, 35(2), 185–189 (1992).

Hibino et al., "Shape-Selectivity over HZSM-5 Modified by Chemical Vapor Deposition of Silicon Alkoxide", *Journal of Catalysis*, 128, 551–558 (1991).

*Primary Examiner*—Asok Pal
*Assistant Examiner*—P. Achutamurthy
*Attorney, Agent, or Firm*—Alexander J. McKillop; Dennis P. Santini; Edward F. Kenehan, Jr.

[57] ABSTRACT

A process for shape selective hydrocarbon conversion that involves contacting a hydrocarbon feedsteam, including ethylbenzene, under conversion conditions with a catalytic molecular sieve which has been modified by being ex situ selectivated with a silicon compound. The ex situ selectivation involves exposing the molecular sieve to at least two silicon impregnation sequences, each sequence comprising an impregnation with a silicon compound followed by calcination. The modified catalyst used in the process may also be steamed. Optionally, the modified catalyst may be trim-selectivated.

30 Claims, No Drawings

SELECTIVE ETHYLBENZENE DISPROPORTIONATION PROCESS (SEBDP) WITH EX SITU SELECTIVATED ZEOLITE CATALYSTS

BACKGROUND OF THE INVENTION

The present invention is directed to a shape selective hydrocarbon conversion process over a modified catalytic molecular sieve. The invention also relates to a modified catalytic molecular sieve and a method for its modification.

The term "shape-selective catalysis" describes unexpected catalytic selectivities in zeolites. The principles behind shape selective catalysis have been reviewed extensively, e.g., by N. Y. Chen, W. E. Garwood and F. G. Dwyer, "Shape Selective Catalysis in Industrial Applications," 36, Marcel Dekker, Inc. (1989). Within a zeolite pore, hydrocarbon conversion reactions such as isomerization, disproportionation, alkylation and transalkylation of aromatics are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in selective ethylbenzene disproportionation to p-diethylbenzene.

The production of para-dialkylbenzene is typically performed by alkylation of alkylbenzene or by alkylbenzene disproportionation over a catalyst under conversion conditions. Such reactions are typified by the reaction of toluene with methanol as described by Chen et al., J. Amer. Chem. Soc. 101, 6783 (1979), and toluene disproportionation, as described by Pines in "The Chemistry of Catalytic Hydrocarbon Conversions", Academic Press, N.Y., 1981, p. 72. These methods typically result in the production of a mixture including para-diethylbenzene, ortho-diethylbenzene, and meta-diethylbenzene. Depending upon the degree of selectivity of the catalyst for para-diethylbenzene (para-selectivity) and the reaction conditions, different percentages of para-diethylbenzene are obtained. The yield, i.e., the amount of diethylbenzene produced as a proportion of the feedstock, is also affected by the catalyst and the reaction conditions.

The equilibrium reaction for the conversion of alkylbenzene to dialkylbenzene and benzene is illustrated by the conversion of toluene to xylene and benzene:

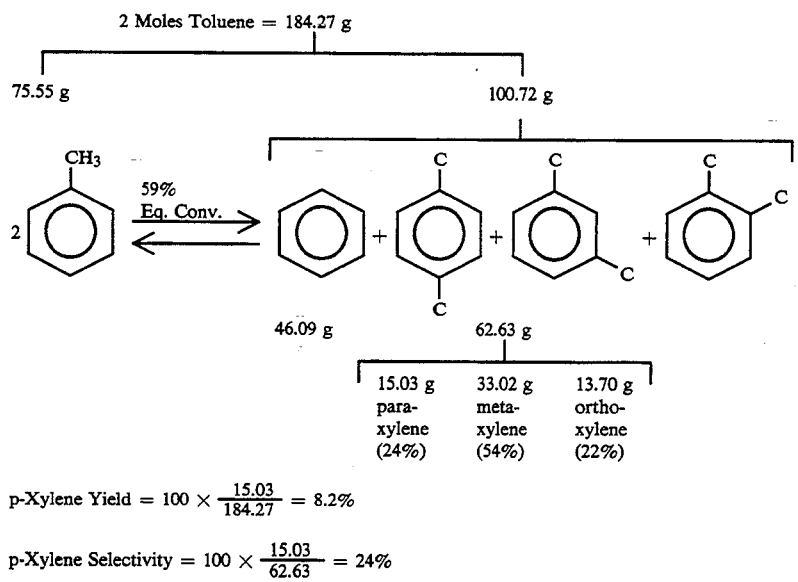

Various methods are known in the art for increasing the para-selectivity of zeolite catalysts. One such method is to modify the catalyst by treatment with a "selectivating agent". For example, U.S. Pat. Nos. 5,173,461, 4,950,835, 4,927,979, 4,465,886, 4,477,583, 4,379,761, 4,145,315, 4,127,616, 4,100,215, 4,090,981, 4,060,568 and 3,698,157 disclose specific methods for contacting a catalyst with a selectivating agent containing silicon ("silicon compound").

U.S. Pat. No. 4,548,914 describes another modification method involving impregnating catalysts with oxides that are difficult to reduce, such as those of magnesium, calcium, and/or phosphorus, followed by treatment with water vapor to improve para-selectivity.

European Patent No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon containing compounds.

Traditionally, ex situ selectivation of zeolites has involved single applications of the modifying compound. It may be noted, however, that the suggestion of multiple treatments was made in U.S. Pat. No. 4,283,306 to Herkes. The Herkes patent discloses the promotion of crystalline silica catalyst by application of a silica source such as tetraethylorthosilicate. The Herkes patent contrasts the performance of catalyst treated once with an tetraethylorthosilicate solution followed by calcination against the performance of catalyst treated twice with tetraethylorthosilicate and calcined after each treatment. The Herkes disclosure shows that the twice-treated catalyst is less active and less selective than the once-treated catalyst as measured by methylation of toluene by methanol, indicating that multiple ex situ selectivation confers no benefit and in fact reduces a catalyst's efficacy in shape-selective reactions.

There has been no suggestion, however, that the selectivation of zeolites by the multiple ex situ impregnation of the zeolites with silicon compounds, followed by calcination after each impregnation would improve the selectivity and activity of the catalysts. It has now been found that a multiple impregnation scheme provides unexpectedly better results in shape-critical hydrocarbon conversions than single silicon impregnation pre-treatment schemes.

It has also now been found that a multiple impregnation scheme provides unexpectedly more efficient deposition of the silicon compound on the catalyst than single silicon impregnation schemes.

Steaming has also been used in the preparation of zeolite catalysts to modify the alpha or improve stability. For example, U.S. Pat. No. 4,559,314 describes steaming a zeolite/binder composite at 200°–500° C. for at least an hour to enhance activity by raising the alpha. U.S. Pat. No. 4,522,929 describes pre-steaming a fresh zeolite catalyst so that the alpha activity first rises then falls to the level of the fresh unsteamed catalyst, producing a stable catalyst which may be used in xylene isomerization. U.S. Pat. No. 4,443,554 describes steaming inactive zeolites (Na ZSM-5) to increase alpha activity. U.S. Pat. No. 4,487,843 describes contacting a zeolite with steam prior to loading with a Group IIIB metal.

It has also now been found that a multiple silicon impregnation scheme for zeolite catalyst selectivation followed by steam treatment produces additional unexpectedly better results than the multiple impregnation pretreatment alone. It has also been found that the optional steam treatment, to be advantageous according to the present invention, must be performed within a limited range of conditions.

Accordingly, it is a purpose of the invention to improve selectivity in catalytic molecular sieves thereby improving shape selectivity in hydrocarbon conversion processes over the molecular sieves.

Various organic compounds have been employed as carriers for silicon compounds in the silicon impregnation methods applied to zeolite catalysts. For example, U.S. Pat. Nos. 4,145,315, 4,127,616, 4,090,981, and 4,060,568 describe the use of inter alia $C_{5-7}$ alkanes as solvents for silicon impregnation.

Selectivation methods have also been described that employ the application of silicon compounds via an aqueous emulsion. Such methods are described in U.S. Pat. Nos. 4,477,583 and 4,127,616.

There has been no suggestion, however, of the use of aqueous carriers for multiple silicon impregnation of zeolites. It has now been found that aqueous carriers, having the advantages of ease and safety of industrial application, unexpectedly provide results that are at least substantially equivalent to those achieved by employment of traditional organic solvents in multiple impregnation selectivation schemes.

Accordingly, it is another purpose of the invention to provide for the use of aqueous carriers, and thereby to improve the ease with which multiple silicon impregnation of zeolite catalysts may be achieved as well as to improve the safety of such methods.

SUMMARY OF THE INVENTION

The invention is a process of shape selective ethylbenzene disproportionation over a modified catalytic molecular sieve by contacting a reaction stream comprising ethylbenzene, under conversion conditions, with a modified catalytic molecular sieve. The modification method includes exposing the catalytic molecular sieve to at least two ex situ selectivation sequences. Each ex situ selectivation sequence includes impregnating the catalytic molecular sieve with a selectivating agent, followed by calcination after each impregnation. Selectivating agents useful in the present invention include a large variety of silicon-containing compounds, preferably silicon polymers soluble in aqueous carriers. Such aqueous carriers include various aqueous solutions, preferably water.

The invention further includes a process of shape selective disproportionation of ethylbenzene by contacting a reaction stream comprising ethylbenzene, under conversion conditions, with a modified catalytic molecular sieve that has been further modified by steaming the modified catalytic molecular sieve at moderate temperatures.

The invention also includes a process of shape selective ethylbenzene disproportionation over a modified catalytic molecular sieve that has been optionally further modified by steaming at moderate temperatures and that has been further modified by in situ trim-selectivating the modified catalytic molecular sieve. The in situ trim-selectivating may be performed by coke trim-selectivating wherein an organic compound is decomposed in the presence of the modified catalytic molecular sieve, at conditions suitable for decomposing the organic compound. Alternatively, the trim-selectivating may be performed by exposing the modified catalytic molecular sieve to a reaction stream that includes a hydrocarbon to be converted and a trim-selectivating agent selected from a group of compounds including a large variety of silicon-containing compounds, at reaction conditions.

Advantageously, the described modified catalysts have enhanced shape selectivity for para-diethylbenzene production. Accordingly, the disproportionation process of the invention exhibits increased selectivity for para-xylene and may exhibit an increased ethylbenzene disproportionation rate constant.

DETAILED DESCRIPTION OF THE INVENTION

The present invention relates to enhanced shape selective production of dialkyl-substituted benzenes, including the shape selective disproportionation of ethylbenzene to commercially useful para-diethylbenzene.

The catalytic molecular sieves useful herein have a Constraint Index from about 1 to about 12 and include intermediate pore zeolites. Zeolites which conform to the specified values of constraint index for intermediate pore zeolites include ZSM-5, ZSM-11, ZSM-5/ZSM-11 intermediate, ZSM-12, ZSM-22, ZSM-23, ZSM-35, ZSM-48, ZSM-50, and ZSM-57. Such zeolites are described, for example, in U.S. Pat. Nos. 3,702,886 and Re. No. 29,949, 3,709,979, 3,832,449, 4,046,859, 4,556,447, 4,076,842, 4,016,245, 4,229,424, 4,397,827, 4,640,849, 4,046,685, 3,308,069 and Re. No. 28,341, to which reference is made for the details of these zeolites.

For the process of the present invention, a zeolite, either incorporated with a binder or in unbound form, is impregnated at least twice, preferably between about two and about six times, with a selectivating agent. The selectivating agent comprises a compound or polymer containing a main group or transition metal, preferably silicon. In each phase of the selectivation treatment, the selectivating agent is deposited on the external surface of the catalyst by any suitable method. For example, a selectivating agent, such as a silicon compound, may be dissolved in a carrier, mixed with the catalyst and then dried by evaporation or vacuum distillation. This method is termed "impregnation". The molecular sieve may be contacted with the silicon compound at a molecular sieve/silicon compound weight ratio of from about 100/1 to about 1/100.

The silicon compound employed may be in the form of a solution, an emulsion, a liquid or a gas under the conditions of contact with a zeolite. Not wishing to be bound by theory, it is believed that the deposited silicon compound extensively covers, and resides substantially exclusively on, the external surface of the molecular sieve. Examples of methods of depositing silicon on the surface of the zeolite are found in U.S. Pat. Nos. 4,090,981, 4,127,616, 4,465,886 and 4,477,583 to Rodewald, which are incorporated by reference herein. Further examples of silicon deposition on zeolite surfaces are described in H. Nakajima, M. Koya, H. Ishida, and M. Kohno, Sekiyu Gakkaishi, 35(2) (1992), and U.S. Pat. No. 4,950,835 to Wang et al.

As was described above the catalysts useful in the present invention are ex situ selectivated by multiple coatings with a high efficiency, para-selectivating agent, each coating followed by calcination and optional trim-selectivation with additional high efficiency para-selectivating agent. As used herein, the term "high efficiency, para-selectivating agent" is used to indicate substances which will increase the para-selectivity of a catalytic molecular sieve to the stated levels in ethylbenzene disproportionation while maintaining commercially acceptable levels of ethylbenzene to para-diethylbenzene conversion.

Such substances include, for example, organic silicon compounds such as phenylmethyl silicone, dimethyl silicone, and blends thereof which have been found to be suitable.

Useful selectivating agents include siloxanes which can be characterized by the general formula:

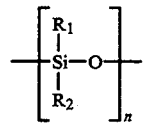

where $R_1$, is hydrogen, halogen, hydroxyl, alkyl, halogenated alkyl, aryl, halogenated aryl, aralkyl, halogenated aralkyl, alkaryl or halogenated alkaryl. The hydrocarbon substituents generally contain from 1 to 10 carbon atoms, preferably methyl or ethyl groups. $R_2$ is independently selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used, as may silicones with other functional groups.

Other, more preferred silicon compounds, including silanes, alkoxy silanes, and organoamine silanes, may also be utilized. These useful silicon-containing selectivating agents include silanes characterizable by the general formula:

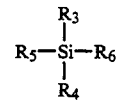

where $R_3$, $R_4$, $R_5$ and $R_6$ are independently selected from the group consisting of hydrogen, hydroxyl, halogen, alkyl, halogenated alkyl, alkoxy, aryl, halogenated aryl, aralkyl, halogenated aralkyl, alkaryl, halogenated alkaryl and organoamine groups. Most preferably $R_3$, $R_4$, $R_5$ and $R_6$ are independently selected from the group consisting of $-N(CH_3)_3$, $-N(C_2H_5)_3$ and $-N(C_3H_7)_3$. Mixtures of these compounds may also be used.

Such compounds are preferred because of their amphiphilic character, allowing their dissolution, or at least emulsification, in aqueous carriers, as well as taking advantage of the hydrophobic character of the zeolite on which the silicon compounds are being deposited.

In the aqueous selectivation systems of the invention, the most preferred silicon selectivating agents include an n-propylamine silane, available as Hydrosil 2627 from Hüls America.

The kinetic diameter of the high efficiency, p-dialkyl aromatic selectivating agent may be larger than the zeolite pore diameter, in order to avoid entry of the selectivating agent into the pore and any concomitant reduction in the internal activity of the catalyst. When a silicon compound is used that is of a size small enough to enter the pores of the catalyst crystal, it is desirable to use the sodium form of the zeolite rather than the hydrogen form.

It has been found that the selectivation method of the invention may be performed on catalyst containing various ions, namely cations. The cations present in the catalyst may be selected from the group consisting of hydrogen, hydrogen precursor, metals of periodic Table Groups IB to VIII, organic cations and combinations thereof. The protection of acid sites in the catalyst has been found to be more effective against degradation by selectivation according to the method of the present invention if the cation is an organic cation such as n-propylamine, or, most preferably, $Na^+$. In particular, $H^+$ and $NH_4^+$ have been found to be less protective of catalyst activity.

When ZSM-5 is treated with a water soluble silane such as Hydrosil, an amino silane polymer, the acid activity of the selectivated catalyst decreases. The amount of activity loss depends upon what form, e.g., H+, Na+, other metal, or organic cation, of the zeolite is treated, according to the method described below. Catalytic testing has shown that the initial acid activity of the selectivated ZSM-5/SiO$_2$ material plays a major role in hydrocarbon conversion activity and selectivity.

U.S. Pat. Nos. 4,060,568, 4,090,981, 4,127,616 and 4,145,315 teach that the silicon compound should be dissolved in a suitable organic solvent then the hydrogen form of ZSM-5 treated with the silicon compound.

It has unexpectedly been found that ex-situ selectivation may be performed using aqueous media as carriers for the selectivating agent. These aqueous media comprise water either alone or in combination with one or more of the compounds of the group including alcohols having between 1 and 18 carbons, glycols, ethers, neutral or charged sulfoxides, neutral or charged amines, aldehydes, ketones, thiophenes, furans, and pyrroles. The media also optionally include any of a large variety of inorganic salts. The most preferred carrier for the selectivating agents of the present invention comprises water.

It has been found that a multiple selectivation scheme provides unexpectedly increased efficiency of deposition of the silicon compound on the surface of the catalyst. This increased efficiency allows for the use of relatively small quantities of the silicon compound as well as relatively small quantities of the aqueous carrier.

Following each deposition of the silicon compound, the catalyst is calcined to decompose the molecular or polymeric species to a solid state species. The catalyst may be calcined at a rate of from about 0.2° C. to about 5° C./minute to a temperature greater than 300° C., but below a temperature at which the crystallinity of the zeolite is adversely affected. Generally, such temperature will be below 600° C. Preferably the temperature of calcination is within the approximate range of 350° C. to 550° C. The product is maintained at the calcination temperature usually for 1 to 24 hours, preferably for between 2 and 6 hours.

The catalyst may be calcined in an atmosphere of N$_2$, an oxygen-containing atmosphere, preferably air, an atmosphere of N$_2$ followed by an oxygen-containing atmosphere, or an atmosphere containing a mixture of N$_2$ and air. Calcination should be performed in an atmosphere substantially free of water vapor, to avoid undesirable uncontrolled steaming of the silicon coated catalyst. The catalyst may be calcined once or more than once after each silicon deposition. The various calcinations in any impregnation sequence need not be identical, but may vary with respect to the temperature, the rate of temperature rise, the atmosphere and the duration of calcination.

Factors upon which the amount of silica incorporated with the zeolite is dependent include temperature, concentration of the silicon compound in the containing medium, the degree to which the zeolite has been dried prior to contact with the silicon compound, and calcination of the zeolite.

After the selectivation sequence, the catalyst is preferably exchanged at least once with NH$_4$+ ions by immersing the catalyst in a solution containing NH$_4$+ ions. Most preferably the concentration of NH$_4$+ ions is approximately 1M. The NH$_4$+ solution may include various inorganic anions, most preferably NO$_3$−. Most preferably, the NH$_4$+ exchange is performed three times.

After the NH$_4$+ exchange sequence, if any, the catalyst may be subjected to steam treatment at a temperature of from about 100° C. to about 600° C., preferably from about 175° C. to about 325° C.; with from about 1% to about 100% steam, preferably from about 50% to about 100% steam; at a pressure of from about 0.01 psia to about 50 psia; for about two to about twelve hours, preferably from about three to about six hours. The selectivated molecular sieve catalyst, with or without binder, can show improved selectivity upon steaming. Alternatively, excessive steaming can be detrimental to a selectivated catalyst.

The selectivated molecular sieve catalyst, with or without binder, can show improved selectivity upon steaming. Alternatively, excessive steaming can be detrimental to a selectivated catalyst.

The alkylbenzene may be fed simultaneously with a second selectivating agent and hydrogen at reaction conditions until the desired p-dialkylbenzene selectivity, e.g., 90%, is attained, whereupon the co-feed of selectivating agent is discontinued. This co-feeding of selectivating agent with alkylbenzene is termed "trim-selectivation". Reaction conditions for this in situ trim-selectivation step generally include a temperature of from about 350° C. to about 540° C. and a pressure of from about atmospheric to about 5000 psig. The reaction stream is fed to the system at a rate of from about 0.1 WHSV to about 20 WHSV. Hydrogen may be fed at a hydrogen to hydrocarbon molar ratio of from about 0.1 to about 20.

The high efficiency para-dialkylbenzene selectivating agent for trim-selectivation may comprise a silicon compound discussed in greater detail above, at a concentration of from about 0.001% to about 10%. For example, organic silicon compounds such as phenylmethyl silicone, dimethyl silicone, and mixtures thereof are suitable. According to one embodiment of the present invention, a silicone containing phenylmethylsilicone and dimethylsilicone groups in a ratio of about 1:1 is co-fed to the system, while the other components, e.g., alkylbenzene and hydrogen, are fed in the amounts set forth above. The high-efficiency para-dialkylbenzene selectivating agent is fed in an amount of from about 0.001 wt. % to about 10 wt. % of the alkylbenzene according to this preferred embodiment. Depending upon the percentage of selectivating agent used, the trim-selectivation will last for at least one hour, preferably about 1 to about 48 hours, most preferably less than 24 hrs.

In this scheme the silicon compound will decompose to deposit additional silica onto the catalyst. During the trim-selectivation procedure the para-selectivity of the catalyst will be observed to increase further. The silicon-containing polymer or molecular species may be dissolved in an alkylbenzene or other appropriate aromatic or hydrocarbon carrier.

Alternatively, the catalyst, prior to contacting with alkylbenzene under disproportionation conditions, may be subjected to trim-selectivation with a thermally decomposable organic compound at an elevated temperature in excess of the decomposition temperature of said compound but below the temperature at which crystallinity of the zeolite is adversely affected. Generally, this temperature will be less than about 650° C. Typically, coke trimming is conducted at conditions outside of the operating parameters used during the main time span of the catalytic cycle.

Organic materials, thermally decomposable under the above temperature conditions to provide coke trimming, encompass a wide variety of compounds including by way of example, hydrocarbons, such a paraffinic, cycloparaffinic, olefinic, cycloolefinic and aromatic; oxygen-containing organic compounds such as alcohols, aldehydes, ethers, ketones and phenols; heterocyclics such as furans, thiophenes, pyrroles and pyridines. Usually, it is contemplated that a thermally decomposable hydrocarbon, such as an alkyl-substituted aromatic, will be the source of coke, most preferably the alkylbenzene being subjected to disproportionation itself. In the latter case, the alkylbenzene is initially brought into contact with the catalyst under conditions of temperature and hydrogen concentration amenable to rapid coke formation. When the desired coke deposition has been effected, the alkyl benzene feed is continued in contact with the coke-containing catalyst under conditions of temperature and hydrogen concentration conducive to disproportionation, with a greatly reduced coking rate.

While not wishing to be bound by theory, it is believed that the advantages of the present invention are in part obtained by rendering acid sites on the external surfaces of the catalyst substantially inaccessible to reactants, while increasing catalyst tortuosity. Acid sites existing on the external surface of the catalyst are believed to isomerize the solution-phase p-diethylbenzene exiting the catalyst pores back to an equilibrium level with the other two isomers, thereby diminishing the catalyst shape selectivity for p-diethylbenzene. By reducing the availability of these acid sites to the solution-phase p-diethylbenzene exiting the pores of the catalyst, the relatively high proportion of the para isomer can be maintained. It is believed that the high-efficiency, para-selectivating agents of the present invention block or otherwise render these external acid sites unavailable to the p-diethylbenzene by chemically modifying said sites.

Disproportionation of Alkyl-Substituted Benzenes

The modified zeolite catalysts described herein are advantageously used in the conversion of aromatic compounds to provide dialkyl-substituted benzene products which are highly enriched in the para-dialkyl-substituted benzene isomer. Conversion reactions of this type include alkylation, transalkylation and disproportionation of aromatics. Alkylations of aromatics in which the catalysts of the invention can be used are described, for example, in U.S. Pat. Nos. 3,755,483, 4,086,287, 4,117,024 and 4,117,026, which are incorporated herein by reference.

The modified catalysts of the present invention have been found to be particularly useful in the selective production of para-dialkyl-substituted benzenes containing alkyl groups of 1 to 4 carbon atoms, such as para-xylene. Such processes are typified by the disproportionation, in the presence of the modified catalyst, of a hydrocarbon precursor, typically a monoalkyl-substituted benzene having 1 to 4 carbon atoms in the alkyl substituent.

As described in U.S. Pat. No. 3,755,483 to Burress, aromatic hydrocarbons such as benzenes, naphthalenes, anthracenes and substituted derivatives thereof, e.g., toluene and xylene, may be alkylated with alkylating agents including olefins such as ethylene, propylene, dodecylene, and formaldehyde, alkyl halides, and alkyl alcohols with 1 to 24 carbons under vapor phase conditions including a reactor inlet temperature up to about 482° C., with a reactor bed temperature up to about 566° C., at a pressure of about atmospheric to about 3000 psig, a mole ratio of aromatic/alkylating agent of from about 1:1 to about 20:1, and a WHSV of 20 to 3000 over ZSM-12 which is a ZSM-5 type catalyst.

As described in U.S. Pat. No. 4,086,287 to Kaeding et al., monoalkylbenzenes having alkyls of 1-2 carbons, such as toluene and ethylbenzene, may be ethylated to produce a para-ethyl derivative, e.g., para-ethyltoluene at a temperature of from about 250° C. to about 600° C., a pressure of 0.1 atmospheres to 100 atmospheres, a weight hourly space velocity (WHSV) of 0.1 to 100, and a ratio of feed/ethylating agent of 1 to 10 over a catalyst having an acid activity, i.e., alpha, of 2 to 5000, modified by pre-coking or combining with oxides of phosphorus, boron or antimony to attain a catalyst with a xylene sorption capacity greater than 1 g/100 g of zeolite and an ortho xylene sorption time for 30% of said capacity of greater than 10 minutes, where sorption capacity and sorption time are measured at 120° C. and a xylene pressure of 4.5±0.8 mm of mercury.

U.S. Pat. No. 4,117,024 to Kaeding describes a process for the ethylation of toluene or ethylbenzene to produce p-ethyltoluene at a temperature of 350° C. to 550° C., a critical pressure of greater than one atmosphere and less than 400 psig, with hydrogen/ethylene ratio of 0.5 to 10 to reduce aging of the catalyst. The zeolite described in U.S. Pat. No. 4,117,024 has a crystal size greater than one micron, and is modified as the catalyst in U.S. Pat. No. 4,086,287 to attain the sorption capacity described in U.S. Pat. No. 4,086,287.

U.S. Pat. No. 4,117,026 to Haag and Olson describes the production of para-dialkyl benzenes having alkyls of 1 to 4 carbons under conditions which vary according to the feed. When the feed includes monoalkyl-substituted benzenes having an alkyl group of 1 to 4 carbons, olefins of 2 to 15 carbons, or paraffins of 3 to 60 carbons or mixtures thereof, conversion conditions include a temperature of 250° C. to 750°, a pressure of 0.1 to 100 atmospheres and a WHSV of 0.1 to 2000. For the disproportionation of toluene, the conditions include a temperature of 400° C. to 700°C., a pressure of 1 to 100 atmospheres and a WHSV of 1-50. When the feed includes olefins of 2 to 15 carbons including cyclic olefins, the conversion conditions include a temperature of 300° C. to 700° C., a pressure of 1 to 100 atmospheres and a WHSV of 1 to 1000. When the feed includes paraffins of 3 to 60 carbons, conditions include a temperature of 300° C. to 700° C. a pressure of 1 to 100 atmospheres and a WHSV of 0.1 to 100. However for lower paraffins of 3 to 5 carbons, the temperature should be above 400° C. When the feed includes mixed aromatics such as ethylbenzene and toluene, and also optionally olefins of 2 to 20 carbons or paraffins of 5 to 25 carbons, conversion conditions include a temperature of 250° C. to 500° C. and a pressure greater than 200 psig. In the absence of added aromatics, the olefins and higher paraffins are more reactive and require lower severity of operation, e.g., a temperature of 250° C. to 600° C., preferably 300° C. to 550° C.

In general, therefore, catalytic conversion conditions over a catalyst comprising the modified zeolite include a temperature of from about 100° C. to about 760° C., a pressure of from about 0.1 atmosphere (bar) to about 200 atmospheres (bar), a weight hourly space velocity of from about 0.08 to about 2000, and a hydrogen/organic, e.g., hydrocarbon compound, mole ratio of from 0 to about 100.

Toluene Disproportionation

The present invention is described in detail below in relation to the disproportionation of alkyl-substituted benzenes, such as toluene and ethylbenzene, over a multiply-selectivated and optionally steamed catalyst. Normally a single pass conversion of an alkylbenzene stream results in a product stream which includes dialkylbenzenes having alkyl groups at all locations, i.e., o-, m-, and p-dialkylbenzenes. A catalyst treated in the manner described herein exhibits a desirable decreased ortho-dialkylbenzene sorption rate parameter and yields a significantly para-selected product from alkylbenzene disproportionation. For example, diffusion rate constants in toluene disproportionation have been discussed by D. H. Olson and W. O. Haag, "Structure-Selectivity Relationship in Xylene Isomerization and Selective Toluene Disproportionation", *Catalytic Materials Relationship Between Structure and Reactivity*, ACS Symposium Ser. No. 248 (1984).

In toluene disproportionation, toluene diffuses into the zeolite with a diffusivity $D_T$. The toluene undergoes disproportionation to p-, m-, and o-xylene and benzene at a total rate constant $k_D$. For high selectivity and catalytic efficiency it is desirable to have:

$$k_D << D_T/r^2.$$

The degree of para-selectivity depends on the activity and the diffusion characteristics of the catalyst. The primary product will be rich in the para isomer if initially produced m- and o-xylene diffuse out of the zeolite crystal at a rate ($D_{m,o}/r^2$) that is lower than that of their conversion to p-xylene ($k_I$), as well as lower than that of the p-xylene diffusion ($D_p/r^2$) out of the catalyst, where:

$D_m$ = diffusion of m-xylene;
$D_o$ = diffusion of o-xylene;
$D_p$ = diffusion of p-xylene;
r = length of diffusion path (crystal size);
$k_1$ = rate of interconversion via isomerization of xylene isomers yielding secondary xylene product m-xylene and o-xylene.

It is desirable to increase the para-selectivity of the catalyst. Practically, this involves decreasing the o- and m-xylene diffusivities such that $$k_I > \frac{D_{m,o}}{r^2}.$$

In such a case the rate of conversion of m- and o-xylenes to p-xylene exceeds the diffusivities of the m- and o-xylenes. As a result, the proportion of the xylene yield that is p-xylene will be increased. Those skilled in the art will appreciate that similar considerations apply to the diffusivities of other alkylbenzenes.

The invention also comprises the near regioselective conversion of ethylbenzene to para-diethylbenzene by disproportionating ethylbenzene in a reaction stream containing a ethylbenzene feed with a selectivated and optionally steamed catalytic molecular sieve, optionally in the presence of hydrogen, and at reaction conditions suitable to provide p-diethylbenzene selectivity of greater than about 80%, preferably greater than 90%. The production stream may also contain small amounts of o- and m-diethylbenzene and trace amounts of impurities such as other alkylbenzenes.

As used herein, the term "para-xylene selectivity" means the proportion of p-xylene, indicated as a percentage, among all of the xylene products, i.e., p-xylene, o-xylene, and m-xylene. Those skilled in the art will appreciate that the relative proximity of the boiling points of these xylene isomers necessitates relatively expensive separation processes for the isolation of p-xylene. On the other hand, p-xylene is more readily separated from other components in the product stream such as benzene, toluene, and p-ethyltoluene.

Furthermore, the dialkylbenzenes are known to proceed in reactions which produce unwanted heavier alkylbenzenes. For example, the xylenes can react to produce unwanted ethylbenzenes (EB) by the following reaction:

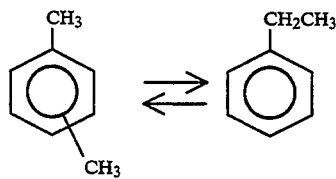

As explained in greater detail herein, the present invention provides a process for obtaining p-diethylbenzene at ethylbenzene conversion rates of at least 15%, preferably at least about 20-25%, with a p-diethylbenzene selectivity of greater than 85%, preferably at least 90%.

The toluene feedstock may also be dried, if desired, in a manner which will minimize moisture entering the reaction zone. Numerous methods known in the art are suitable for drying the toluene charge for the process of the invention. These methods include percolation through any suitable desiccant, for example, silica gel, activated alumina, molecular sieves or other suitable substances, or the use of liquid charge dryers.

The catalytic molecular sieves useful for the invention are preferably in the hydrogen form but may be in the ammonium or sodium form and preferably comprise an intermediate pore-size zeolite such as a ZSM-5, ZSM-11, ZSM-22, ZSM-23, or ZSM-35 as discussed above. The catalytic molecular sieves also preferably have a Constraint Index of about 1–12. The details of the method by which Constraint Index is determined are described fully in U.S. Pat. No. 4,016,218, incorporated herein by reference.

The crystal size of zeolites used herein is preferably greater than 0.1 micron. The accurate measurement of crystal size of zeolite materials is frequently very difficult. Microscopy methods such as SEM and TEM are often used, but these methods require measurements on a large number of crystals and for each crystal measured, values may be required in up to three dimensions. For ZSM-5 materials described in the examples below, estimates were made of the effective average crystal size by measuring the rate of sorption of 2,2-dimethylbutane at 90° C. and 60 torr hydrocarbon pressure. The crystal size is computed by applying the diffusion equation given by J. Crank, "The Mathematics of Diffusion", Oxford at the Clarendon Press, 1957, pp 52–56 for the rate of sorbate uptake by a solid whose diffusion properties can be approximated by a plane sheet model. In addition, the diffusion constant of 2,2-dimethylbutane, D, under these conditions is taken to be $1.5 \times 10^{-14}$ cm$^2$/sec. The relation between crystal size measured in microns, d, and diffusion time measured in minutes, $t_{0.3}$, the time required for the uptake of 30% of capacity of hydrocarbon, is:

$$d = 0.0704 \times t_{0.3}^{\frac{1}{2}}.$$

In the present case these measurements have been made on a computer controlled, thermogravimetric electrobalance, but there are numerous ways one skilled in the art could obtain the data. The larger crystal material used herein has a sorption time, $t_{0.3}$, of 497 minutes, which gives a calculated crystal size of 1.6 microns. The smaller crystal material has a sorption time of 7.8 minutes, and a calculated crystal size of 0.20 micron.

The "alpha value" of a catalyst is an approximate indication of the catalytic cracking activity of the catalyst compared to a standard catalyst, and it gives the relative rate constant (rate of normal hexane conversion per volume of catalyst per unit time). It is based on the activity of the amorphous silica-alumina cracking catalyst taken as an alpha of 1 (Rate Constant=0.016 sec$^{-1}$). The alpha test is described in U.S. Pat. No. 3,354,078 and in *The Journal of Catalysis*, Vol. 4, pp. 522–529 (August 1965); Vol. 6, p. 278 (1966); and Vol. 61, p. 395 (1980), each incorporated herein by reference as to that description. It is noted that intrinsic rate constants for many acid-catalyzed reactions are proportional to the alpha value for a particular crystalline silicate catalyst (see "The Active Site of Acidic Aluminosilicate Catalysts," *Nature*, Vol. 309, No. 5959, pp. 589–591, Jun. 14 1984). The experimental conditions of the test used herein include a constant temperature of 538° C. and a variable flow rate as described in detail in the *Journal of Catalysis*, Vol. 61, p. 395 (1980). The catalyst in the present invention preferably has an alpha value greater than 1, for example, from about 1 to about 2000. The alpha value of the catalyst may be increased by initially treating the catalyst with nitric acid or by mild steaming before selectivation. This type of steaming is discussed in U.S. Pat. No. 4,326,994.

The silica to alumina ratio of the catalysts of the invention may be determined by conventional analysis. This ratio is meant to represent, as closely as possible, the ratio in the rigid atomic framework of the zeolite crystal and to exclude aluminum in the binder or in cationic or other form within the channels. Although zeolites with a silica to alumina ratio of up to about 100 are useful, it is preferred to use zeolites having ratios from about 20 to about 80.

After activation, such zeolites acquire an intra-crystalline absorption capacity for normal hexane which is greater than that for water, i.e., they exhibit "hydrophobic" properties. This hydrophobicity property would indicate that a suitable medium for the silicon compound used herein should be organic, e.g. n-hexane, benzene, toluene, chloroform, etc., and not water. If an organic medium were to be used, the silicon compound would be dissolved therein and the hydrophobic properties of the zeolite would not work against deposition of the silicon compound on the zeolite. However, it has unexpectedly been found that an aqueous carrier of a silicon compound is useful for the deposition of the silicon compound on the zeolite.

The economic advantages accompanying the present method for catalyst preparation are numerous, when compared to preparing such a catalyst via contact with an organic solution of a silicon compound. For example, water vapor can be vented to the atmosphere while organic vapor can not. The use of water in pure form or as part of a multicomponent carrier system, containing other chemicals listed above, has unexpectedly been found to permit effective ex situ selectivation of catalytic molecular sieves. The use of aqueous media in place of organic solvents, when a "suitable solvent" is required by the prior art for "dissolving" a particular compound which is not soluble in water, is an economic advantage which is not so readily apparent. Clearly, and unexpectedly, the use of a water carrier in place of an organic solvent in treatment of a hydrophobic crystalline zeolite to produce even an equivalent product is an advantage which would not be readily apparent.

For the improved disproportionation process of this invention, the suitable molecular sieve may be employed in combination with a support or binder material such as, for example, a porous inorganic oxide support or a clay binder. While the preferred binder is silica, other non-acidic binder materials may be employed, generally in the form of dried inorganic oxide gels or gelatinous precipitates. Suitable clay materials include, by way of example, bentonite and kieselguhr. The relative proportion of suitable crystalline molecular sieve to the total composition of catalyst and binder or support may be from about 30% to about 98% by weight and is preferably from about 50% to about 80% by weight of the composition. The composition may be in the form of an extrudate, beads or fluidizable microspheres.

Operating conditions employed in the process of the present invention will affect the para-selectivity and ethylbenzene conversion rate. Such conditions include the temperature, pressure, space velocity, molar ratio of the reactants, and the hydrogen to hydrocarbon mole ratio (H$_2$/HC). For example, it has been observed that an increase in temperature can increase the activity of the modified catalyst. It has also been observed that an increased space velocity (WHSV) can enhance the para-selectivity of the modified catalyst in alkylbenzene disproportionation reactions. This characteristic of the modified catalyst allows for substantially improved throughput when compared to current commercial practices. In addition, it has been observed that the disproportionation process may be performed using H$_2$ as a diluent, thereby dramatically increasing the cycle length of the catalyst.

A selectivated and steamed catalytic molecular sieve may be contacted with a toluene feedstock under conditions for effecting vapor-phase disproportionation. Conditions effective for accomplishing the high para-selectivity and acceptable toluene disproportionation conversion rates include a reactor inlet temperature of from about 200° C. to about 600° C., preferably from about 350° C. to about 500° C.; a pressure of from about atmospheric to about 5000 psig, preferably from about 100 to about 1000 psig; a WHSV of from about 0.1 to about 20, preferably from about 2 to about 10; and a H$_2$/HC mole ratio of from about 0.05 to about 20, preferably from about 0.1 to about 6. This process may be conducted in either batch or fluid bed operation, with the attendant benefits of either operation readily obtainable. The effluent may be separated and distilled to remove the desired product, i.e., p-dialkylbenzene, as well as other by-products. Alternatively, the C$_8$ fraction may be subjected to further separation, in the case of xylenes, subjected to the PAREX process or crystallization to yield p-xylene.

The catalyst may be further modified in order to reduce the amount of undesirable by-products, particularly ethylbenzene. The state of the art is such that the reactor effluent from standard toluene disproportionation typically contains about 0.5% ethylbenzene by-product. Upon distillation of the reaction products, the level of ethylbenzene in the $C_8$ fraction often increases to between about 3% and 4%. This level of ethylbenzene is unacceptable for polymer grade p-xylene since ethylbenzene in the $C_8$ product, if not removed, degrades the quality of fibers ultimately produced from the p-xylene product. Consequently, ethylbenzene content of the p-xylene fraction must be kept low. Ethylbenzene can be substantially removed by crystallization, isomerization or by superfractionation processes. Removal of the ethylbenzene by conventional isomerization is impractical when the xylene stream includes greater than 70% or 80% p-xylene, since the p-xylene would be concurrently isomerized to equilibrium xylenes, thereby reducing the amount of p-xylene in the xylene stream. It is known in the art that the alternative procedure of removing the ethylbenzene by superfractionation is extremely expensive.

In order to avoid the need for downstream ethylbenzene removal, the level of ethylbenzene by-product is advantageously reduced by incorporating a hydrogenation/ dehydrogenation function within the catalyst, such as by addition of a metal compound such as platinum. While platinum is the preferred metal, other metals of Groups IB to VIII of the Periodic Table such as palladium, nickel, copper, cobalt, molybdenum, rhodium, ruthenium, silver, gold, mercury, osmium, iron, zinc, cadmium, and mixtures thereof, may be utilized. The metal may be added by cation exchange, in amounts of from about 0.01% to about 2%, typically about 0.5%. It is desirable that the metal be able to enter the pores of the catalyst. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum-(II) chloride. The metallic compound advantageously enters the pores of the catalyst. The catalyst can then be filtered, washed with water and calcined at temperatures of from about 250° C. to about 500° C. It will be appreciated by those skilled in the art that similar considerations apply to processing involving other alkylbenzenes.

The following non-limiting Examples illustrate the invention in relation to the disproportionation of toluene as well as in relation to the similar disproportionation of ethylbenzene.

In the Examples, the o-xylene sorption rate parameter $D_o/r^2$ was measured at 120° C. and 3.8 torr.

$D_o$ = diffusivity of o-xylene r = crystal size $D_o/r^2$ = the diffusion parameter which expresses the rate of o-xylene movement into and out of the crystalline phase Comparative examples (Examples 1–5) are described below for catalyst preparation and evaluation. Examples 1–5 are for single selectivations, but catalyst's activity decreases to a much larger extent when HZSM-5 is treated multiple times.

EXAMPLE 1

A propylamine silane polymer (Hydrosil 2627) was diluted with deionized (DI) water at a 1:1 weight ratio. HZSM-5/SiO$_2$ (Si/Al$_2$=26:1), with a crystal size of 0.20 micron, was immersed overnight in the silane polymer/water solution by impregnation. The sample was then calcined at 538° C. in nitrogen followed by air. A small amount of calcined material was exchanged with 1M NH$_4$NO$_3$ at room temperature to determine the number of framework aluminum sites which remain after selectivation. A sample of the parent HZSM-5/SiO$_2$ material contained 0.76 milliequivalent/gram (meq/g) acid sites, while the selectivated material contained 0.29 meq/g acid sites.

EXAMPLE 2

10 grams of HZSM-5/SiO$_2$ (Si/Al$_2$=26:1), having a crystal size of 0.20 micron, was exchanged twice with 650 ml of 0.012N NaOH at room temperature for one hour. To examine the extent of sodium exchange, 0.1 g of NaZSM-5/SiO$_2$ was treated with NH$_3$ gas then refluxed in DI H$_2$O for one hour, filtered and dried at 130° C. The number of acid sites remaining, i.e., not exchanged with a sodium cation, was 0,017 meq/g.

A propylamine silane polymer (Hydrosil 2627) was diluted with deionized water at a 2:1 weight ratio. The Na-ZSM-5/SiO$_2$ was then treated with the silane polymer/water solution by column exchange. The sample was then calcined at 538° C. in nitrogen followed by air. The calcined material was exchanged with 1M NH$_4$NO$_3$ at room temperature to determine the number of acid sites which remained after selectivation. NH$_3$-TPAD showed 0.62 meq/g of acid sites remained compared to 0.76 meq/g prior to selectivation.

EXAMPLE 3

10 grams of HZSM-5/SiO$_2$ (Si/Al$_2$=26:1) having a crystal size of 0.20 micron was exchanged with 1M NH$_4$NO$_3$ at room temperature for one hour until at least 75% of the framework aluminum sites are exchanged with NH$_4^+$ cations as measured by NH$_3$-TPAD.

A propylamine silane polymer (Hydrosil 2627) was diluted with deionized water at a 1:1 ratio. The NH$_4$-ZSM-5/SiO$_2$ was then immersed overnight in the Hydrosil 2627/water solution. The sample was then calcined at 538° C. in nitrogen followed by air. A small amount of calcined material was exchanged with 1M NH$_4$NO$_3$ at room temperature to determine the number of framework aluminum sites which remained after selectivation. The number of acid sites had decreased from 0.76 to 0.22 meq/g.

EXAMPLE 4

10 grams of HZSM-5/SiO$_2$, (Si/Al$_2$=26:1), having a crystal size of 0.2 micron, was exchanged with a 2% n-propylamine/H$_2$O solution at room temperature for one hour until at least 75% of the framework aluminum sites were exchanged with n-propylamine cations as measured by NH$_3$-TPAD.

A propylamine silane polymer (Hydrosil 2627) solution was diluted with deionized water at amino silane/water weight ratio of 2:1. The n-propylamine-ZSM-5/SiO$_2$ was then immersed overnight in the amino silane/water solution. The sample was then calcined at 538° C. in nitrogen followed by air. A small amount of calcined material was exchanged with 1M NH$_4$NO$_3$ at room temperature to determine the number of framework aluminum sites which remained after selectivation. The number of acid sites decreased from 0.76 meq/g to 0.39 meq/g.

Examples 1–4 above demonstrate that, to maintain a high number of acid sites according to the present invention, it is necessary to protect the acid sites with a cation, most preferably Na+ or preferably an organic cation, rather than H+ or NH4+.

EXAMPLE 5

Twenty grams of an n-propylamine silane polymer (Hydrosil 2627), was diluted with 20 grams deionized water. Seven grams of NaZSM-5/SiO2 was added to this solution and allowed to equilibrate for 16 hours, after which the remaining water was evaporated at 130° C. The sample was then calcined in N2 at 2° C./min to 538° C. for two hours, followed by calcination in air at 538° C. for two hours. 16.8% SiO2 was found to have been added to the extrudate. The catalyst was tested for toluene disproportionation as described below.

Catalytic evaluation of the selectivated catalyst was conducted at atmospheric pressure, 482° C. and 4% toluene conversion. The p-xylene selectivity was 31% at these conditions.

EXAMPLE 6

Fifteen grams of NaZSM-5A/SiO2 was added to 15 grams of an amino silane polymer/water solution and allowed to stand until dry. The catalyst was then heated in N2 at 2° C./min to 538° C. then held for two hours. The sample was cooled to 300° C., air introduced and the sample heated at 2° C./min to 538° C. and held for two hours. Based on the known silicon content of the n-propylamine silane polymer (Hydrosil 2627), 4.5% SiO2 was found to have been added to the extrudate.

The once-modified catalyst was treated a second time using the procedure described for the first modification.

Thirteen grams of the twice-modified catalyst was added to 13 grams of a 27% amino silane polymer/water solution and allowed to stand until dry. The catalyst was then heated in N2 at 2° C./min to 538° C. then held for two hours. The sample was cooled to 300° C., air introduced and the sample heated at 2° C./min to 538° C. and held for two hours.

Ten grams of the triply-treated catalyst was added to 10 grams of a 27% amino silane polymer/water solution and allowed to stand until dry. The catalyst was then heated in N2 at 2° C./min to 538° C. then held for two hours. The sample was cooled to 300° C., air introduced and the sample heated at 2° C./min to 538° C. and held for two hours.

After the fourth modification, the sample was exchanged with 1M NH4NO3 at room temperature for one hour for a total of three exchanges.

Catalytic evaluation of the quadruply-treated catalyst (0.77 grams ash weight) was conducted in an automated unit with on line sampling. The sample was loaded into a 0.305" stainless steel tube reactor and then air calcined at 538° C. for two hours to convert the ammonium form to the hydrogen form of ZSM-5. The sample was cooled to 300° C. in nitrogen to remove excess oxygen. The sample was then heated in hydrogen at 3.5° C./min to 425° C. in 40 cc/min hydrogen. Pure toluene was introduced at 425° C. at 4 WHSV, 2 H2/HC and 500 psig. To determine the activity/selectivity performance of the selectivated catalyst, reactor temperature and toluene feed rate were varied to change toluene conversion. Representative toluene conversion, p-xylene selectivity and a product yield data are shown in Table I.

TABLE I

| Product Yields for Toluene Disproportionation | | | | |
|---|---|---|---|---|
| WHSV, hr−1 | 4 | 8 | 12 | 16 |
| Products (wt. %) | | | | |
| C5− | 2.0 | 0.9 | 0.5 | 0.3 |
| Benzene | 16.5 | 10.9 | 7.9 | 6.0 |
| Ethylbenzene | 0.5 | 0.3 | 0.1 | 0.1 |
| p-Xylene | 8.1 | 8.3 | 7.2 | 6.0 |
| Total xylenes | 16.2 | 12.4 | 9.4 | 7.4 |
| C9+ | 0.8 | 1.0 | 0.3 | 0.3 |
| Toluene Conversion, wt % | 35.9 | 24.9 | 18.3 | 14.1 |
| p-Xylene Selectivity, % | 50.3 | 67.2 | 75.8 | 80.7 |
| Reaction Conditions: | T = 446° C., | 4–16 WHSV, | 2 H2/HC, | 500 psig |

80.7% p-xylene selectivity was observed at 14.1% toluene conversion for the quadruply-treated catalyst, compared to 31% p-xylene selectivity at 4% toluene conversion for the singly treated catalyst of Example 5. As shown in Example 6 and ACS Symposium Series No. 248 (1984), p-xylene selectivity increases as toluene conversion decreases. Therefore, at 14% toluene conversion, the p-xylene selectivity of the singly treated catalyst will not be higher than 31%.

EXAMPLE 7

A multiple selectivation procedure for a water based system is described below. The catalyst described in this example was selectivated in the sodium form using Hydrosil 2627, a water soluble n-propylamine silane polymer.

Ten grams of NaZSM-5/SiO2 extrudate, with a crystal size of 0.20 micron, was added to 11 grams of a 16% solution of the n-propylamine silane polymer (Hydrosil 2627) in water and allowed to stand until dry. The catalyst was then heated in N2 at 2° C./min. to 538° C. then held for two hours. The sample was cooled to 300° C., air introduced and the sample heated at 2° C./min. to 538° C. and held for two hours. Based on the silicon content of the silane polymer, 2.9 wt. % SiO2 was added to the extrudate.

Ten grams of the once-modified catalyst was added to 11 grams of a 16% solution of the n-propylamine silane polymer (Hydrosil 2627) in water and allowed to stand until dry. The catalyst was then heated in N2 at 2° C./min. to 538° C. then held for 2 hours. The sample was cooled to 300° C., air introduced and the sample heated at 2° C./min. to 538° C. and held for two hours. Based on the silicon content of the silane polymer, 2.9 wt. % SiO2 was added to the extrudate, for 5.9 wt. % total added silica.

Two grams of the twice-modified catalyst was added to 2.5 grams of a 16% solution of the n-propylamine silane polymer (Hydrosil 2627) in water solution and allowed to stand until dry. The catalyst was then heated in N$_2$ at 2° C./min. to 538° C. then held for two hours. The sample was cooled to 300° C., air introduced and the sample heated at 2° C./min. to 538° C. and held for two hours. Based on the silicon content of the silane polymer, 3.3 wt. % SiO$_2$ was added to the extrudate, for 9.4 wt. % total added silica.

Two grams of the triply-modified catalyst was added to 2.5 grams of a 16% solution of the n-propylamine silane polymer (Hydrosil 2627) in water solution and allowed to stand until dry. The catalyst was then heated in N$_2$ at 2° C./min. to 538° C. then held for two hours. The sample was cooled to 300° C., air introduced and the sample heated at 2° C./min. to 538° C. and held for two hours. Based on the silicon content of the silane polymer, 3.3 wt. % SiO$_2$ was added to the extrudate, for 13.0 wt. % total added silica.

After the fourth modification, the sample was exchanged with 1M NH$_4$NO$_3$ at room temperature for one hour for a total of three exchanges.

Catalytic evaluation of the modified catalyst (0.783 grams ash weight) was conducted as described in Example 6. The modified catalyst exhibited 92% p-xylene and 14.2% conversion at 446° C., 16 WHSV, 2H$_2$/HC, 500 psig.

EXAMPLE 8

Eleven grams of NaZSM-5/SiO$_2$ with a crystal size of 0.20 micron, was added to 11 grams of a 21% n-propylamine silane polymer (Hydrosil 2627)/water solution and allowed to stand until dry. The catalyst was then heated in N$_2$ at 2° C./min to 538° C. then held for two hours. Based on the silicon content of the Hydrosil 2627, 3.6 wt. % SiO$_2$ was added to the extrudate.

The procedure described for the first modification was repeated.

Eight grams of the twice-treated catalyst was added to 8 grams of a 21% n-propylamine silane polymer (Hydrosil 2627)/ water solution and allowed to stand until dry. The catalyst was then heated in N$_2$ at 2° C./min to 538° C. then held for two hours. The sample was cooled to 300° C., air was introduced and the sample was heated at 2° C./min to 538° C. and held for two hours.

Six grams of the three times-treated catalyst was added to 6 grams of a 21% n-propylamine silane polymer (Hydrosil 2627)/water solution and allowed to stand until dry. The catalyst was then heated in N$_2$ at 2° C./min to 538° C. then held for two hours. The sample was cooled to 300° C., air was introduced and the sample was heated at 2° C./min to 538° C. and held for two hours.

After the fourth modification, the sample was exchanged with 1M NH$_4$NO$_3$ at room temperature for one hour for a total of three exchanges. The sample was then air calcined at 538°C. for two hours followed by steaming at 430° C. for four hours with 100% H$_2$O(g).

The above catalyst was tested for ethylbenzene disproportionation at 6 WHSV, 30 psig, 315–330° C. and 14% ethylbenzene conversion. The p-diethylbenzene selectivity was greater than 98% which is higher than conventional catalysts.

EXAMPLE 9

Ten grams of NaZSM-5/SiO$_2$ was added to 10 grams of a 50% n-propylamine silane polymer (Hydrosil 2627)/water solution and allowed to stand until dry. The catalyst was then heated in N$_2$ at 2° C./min to 538° then held for two hours. The sample was cooled to 300° C., air was introduced, and then heated at 2° C./min to 538° C. and held for two hours.

9.5 grams of the once-modified catalyst was added to 9.5 grams of a 70% n-propylamine silane polymer (Hydrosil 2627)/water solution and allowed to stand until dry. The catalyst was then heated in N$_2$ at 2° C./min to 538° C., then held for two hours. The sample was cooled to 300° C., air introduced and then heated at 2° C./min to 538°, and held for two hours. After the second modification, the sample was exchanged with 1M NH$_4$NO$_3$ at room temperature for one hour for a total of three exchanges, then air calcined at 538° C. for two hours.

Catalytic evaluation of the twice-modified catalyst was conducted as described in Example 5. Representative selectivity/conversion data are shown in Table 2.

The sample was then coke trimmed to determine if higher p-xylene selectivity could be obtained. The reactor temperature was raised to 540° C., the feed rate to 6.5 WHSV, H$_2$/HC decreased to 0.5, nitrogen added at 3.5 N$_2$/HC and pressure decreased to 400 psig. After 15 hours at these conditions, the reactor was set at 456° C., 4 WHSV, 2 H$_2$/HC and 500 psig. Representative selectivity/conversion data are shown in Table 2. When the data before and after coke selectivation are compared, higher p-xylene selectivity is observed for the coke trimmed catalyst at a given toluene conversion.

TABLE 2

|  | Ex Situ Selectivated Catalyst | | Coke Trimmed Ex Situ Selectivated Catalyst | |
| --- | --- | --- | --- | --- |
| Temperature °C. | 447 | 447 | 455 | 455 |
| WHSV, hr$^{-1}$ | 7.9 | 15.8 | 3.9 | 3.9 |
| H$_2$/HC | 2.0 | 2.0 | 2.0 | 2.0 |
| Pressure, psig | 500 | 500 | 500 | 500 |
| Products, wt % | | | | |
| C$_5$$^-$ | 0.5 | 0.2 | 0.9 | 1.5 |
| Benzene | 9.9 | 6.3 | 5.8 | 10.7 |
| Ethylbenzene | 0.2 | 0.1 | 0.1 | 0.4 |
| p-Xylene | 4.6 | 3.6 | 5.5 | 7.4 |
| Total xylenes | 12.4 | 7.9 | 7.4 | 12.2 |
| C$_9$$^+$ | 0.5 | 0.3 | 0.3 | 0.6 |
| Toluene Conversion, wt % | 23.5 | 14.8 | 14.6 | 25.4 |
| p-Xylene Selectivity, % | 37 | 46 | 74 | 61 |

While the invention has been described with reference to specific embodiments, it will be apparent that numerous variations, modifications and alternative embodiments of the invention are possible, and accordingly all such variations, modifications, and alternative embodiments are to be regarded as being within the spirit and scope of the present invention as claimed.

What is claimed is:

1. A process for enhanced shape selective disproportionation of ethylbenzene comprising:
   Contacting a reaction stream comprising ethylbenzene, under disproportionation conditions, with a catalytic molecular sieve which has been modified by being exposed to at least two ex situ selectivation sequences, wherein the ex situ selectivation sequence includes the steps of contacting the catalytic molecular sieve with a water-soluble organoamine silane polymer dissolved in an aqueous carrier and subsequently calcining the catalytic molecular sieve.

2. The process of claim 1, wherein the conversion conditions comprise a temperature of from about 100°

C. to about 760° C., a pressure of from about 0.1 atmosphere to about 200 atmospheres, and a weight hourly space velocity of from about 0.08 to about 200.

3. The process of claim 1, wherein the catalytic molecular sieve has been modified by between two and six ex situ selectivation sequences.

4. The process of claim 1, wherein the catalytic molecular sieve has been modified by two ex situ selectivation sequences.

5. The process of claim 1, wherein the cataleptic molecular sieve has been modified by three ex situ selectivation sequences.

6. The process of claim 1, wherein the water-soluble organoamine silane polymer comprises n-propylamine silane polymer.

7. The process of claim 1, wherein the aqueous carrier comprises water and a compound selected from the group consisting of inorganic salts, alcohols having between 1 and 18 carbons, glycols, ethers, neutral or charged sulfoxides, neutral or charged amines, aldehydes, ketones, thiophenes, furans, pyrroles and mixtures thereof.

8. The process of claim 1, wherein the aqueous carrier comprises water.

9. The process of claim 1, wherein the aqueous carrier consists essentially of water.

10. The process of claim 1, wherein the catalytic molecular sieve comprises a zeolite having a Constraint Index from about 1 to about 12.

11. The process of claim 1, wherein the catalytic molecular sieve comprises ZSM-5.

12. The process of claim 11, wherein the catalytic molecular sieve comprises ZSM-5 having a crystal size larger than about 0.2 micron.

13. The process of claim 11 wherein the catalytic molecular sieve comprises ZSM-5 having a crystal size of about 0.2 micron or smaller.

14. The process of claim 1, wherein the catalytic molecular sieve contains an ion selected from the group consisting of hydrogen, hydrogen precursor, metals of Periodic Table Groups IB to VIII, organic cations, and combinations thereof.

15. The process of claims 14, wherein the ion comprises $Na^+$.

16. The process of claim 14, wherein the ion comprises n-propylamine cation.

17. The process of claim 1, wherein the catalytic molecular sieve is incorporated with binder before being modified.

18. The process of claim 17, wherein the binder is $SiO_2$.

19. The process of claim 1, wherein the catalytic molecular sieve is incorporated with binder after being modified.

20. The process of claim 19, wherein the binder is $SiO_2$.

21. The process of claim 1, wherein the catalytic molecular sieve is modified in an as-synthesized condition.

22. The process of claim 1, wherein the catalytic molecular sieve has been further modified by being contacted with steam under conditions comprising from about 1% to about 100% water vapor, a temperature of from about 100° C. to about 600° C., a pressure of from about 0.01 to about 50 psig, for a time of from about 0.1 to about 12 hours.

23. The process of claim 1, wherein the modified catalytic molecular sieve has been further modified by the step of in situ trim-selectivating the modified catalytic molecular sieve.

24. The process of claim 23, wherein the in situ trim-selectivating step comprises contacting the modified catalytic molecular sieve with a thermally decomposable organic compound selected from the group consisting of paraffins, cycloparaffins, olefins, cycloolefins, aromatics, alcohols, aldehydes, ethers, ketones, phenols, heterocyclics, and mixtures thereof at a temperature in excess of the decomposition temperature of the thermally decomposable organic compound.

25. The process of claim 24, wherein the organic compound is ethylbenzene.

26. The process of claim 23, wherein the in situ trim-selectivating step comprises contacting the modified catalytic molecular sieve with a reaction stream comprising ethylbenzene and a trim-selectivating agent.

27. The process of claim 26, wherein the trim-selectivating agent is selected from the group consisting of silicones, silicone polymers, silanes, and alkoxysilanes.

28. The process of claim 26, wherein the trim-selectivating agent is selected from the group consisting of $$\left[ \begin{array}{c} R_1 \\ | \\ Si-O \\ | \\ R_2 \end{array} \right]_n,$$

wherein $R_1$ and $R_2$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl, and n is between 2 and 1000; and $$R_5-\underset{\underset{R_4}{|}}{\overset{\overset{R_3}{|}}{Si}}-R_6,$$

wherein $R_3$, $R_4$, $R_5$ and $R_6$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl.

29. The process of claim 26, wherein the trim-selectivating agent comprises dimethylphenylmethyl polysiloxane.

30. The process of claim 2, wherein the conversion conditions further comprise a hydrogen/hydrocarbon mole ratio of from greater than 0 to about 100.

* * * * *

UNITED STATES PATENT AND TRADEMARK OFFICE
CERTIFICATE OF CORRECTION

PATENT NO. : 5,382,737
DATED : January 17, 1995
INVENTOR(S) : J.S. Beck et al.

It is certified that error appears in the above-indentified patent and that said Letters Patent is hereby corrected as shown below:

Col. 21, claim 2, line 3, "200" should be --2000--.

Col. 21, claim 5, line 10, "cataleptic" should be --catalytic--.

Signed and Sealed this

Ninth Day of May, 1995

*Attest:*

BRUCE LEHMAN

*Attesting Officer*  *Commissioner of Patents and Trademarks*